United States Patent [19]

McEwen et al.

[11] Patent Number: 5,030,341

[45] Date of Patent: Jul. 9, 1991

[54] APPARATUS FOR SEPARATING PHASES OF BLOOD

[75] Inventors: James A. McEwen, Richmond; William J. Godolphin, Vancouver; Rainer M. Bohl, Vancouver; Mark N. Dance, Vancouver; Marty L. Furse, Vancouver; John C. Osborne, Port Coquitlam, all of Canada

[73] Assignee: Andronic Technologies, Inc., Canada

[21] Appl. No.: 346,063

[22] Filed: May 2, 1989

Related U.S. Application Data

[63] Continuation-in-part of Ser. No. 192,847, May 11, 1988, abandoned, which is a continuation of Ser. No. 33,769, Apr. 3, 1987, Pat. No. 4,828,716.

[51] Int. Cl.$^5$ .............................................. B01D 21/26
[52] U.S. Cl. ..................................... 210/94; 210/515; 210/516; 210/518; 222/92; 222/188; 222/490
[58] Field of Search ................. 210/94.95, 514, 515, 210/516, 518; 422/101, 102; 222/92, 188, 490

[56] References Cited

U.S. PATENT DOCUMENTS

| | | | |
|---|---|---|---|
| 3,782,548 | 1/1974 | Bowen | 210/94 |
| 3,929,646 | 12/1975 | Adler | 210/516 |
| 3,941,699 | 3/1976 | Ayres | 210/516 |
| 4,001,122 | 1/1977 | Griffin | 210/516 |
| 4,021,352 | 5/1977 | Sarstedt | 210/359 |
| 4,202,769 | 5/1980 | Greenspan | 210/516 |
| 4,203,840 | 5/1980 | Stoeppler et al. | 210/513 |
| 4,350,585 | 9/1982 | Johansson et al. | 210/94 |

FOREIGN PATENT DOCUMENTS

| | | |
|---|---|---|
| 0035396A3 | 9/1981 | European Pat. Off. . |
| 0098150A3 | 1/1984 | European Pat. Off. . |
| 1806196 | 7/1969 | Fed. Rep. of Germany . |
| 2816870A1 | 10/1978 | Fed. Rep. of Germany . |
| 3301113A1 | 7/1984 | Fed. Rep. of Germany . |

Primary Examiner—W. Gary Jones
Attorney, Agent, or Firm—Klarquist, Sparkman, Campbell, Leigh, and Whinston

[57] ABSTRACT

Apparatus for partitioning a pre-selected phase of a sample of liquid, such as blood, having a plurality of phases of differing densities. Disclosed is an apparatus for separating a pre-selected phase of a sample contained in an enclosed chamber, wherein said apparatus can be used with a separating means which rotates the chamber about either a longitudinal axis of the chamber, or about an axis perpendicular to the longitudinal axis of the chamber and not passing through the chamber. In addition, separating means in which such an enclosed chamber is rotated about a longitudinal axis is described. Also disclosed is an apparatus for dispensing fluid from said enclosed chamber.

6 Claims, 11 Drawing Sheets

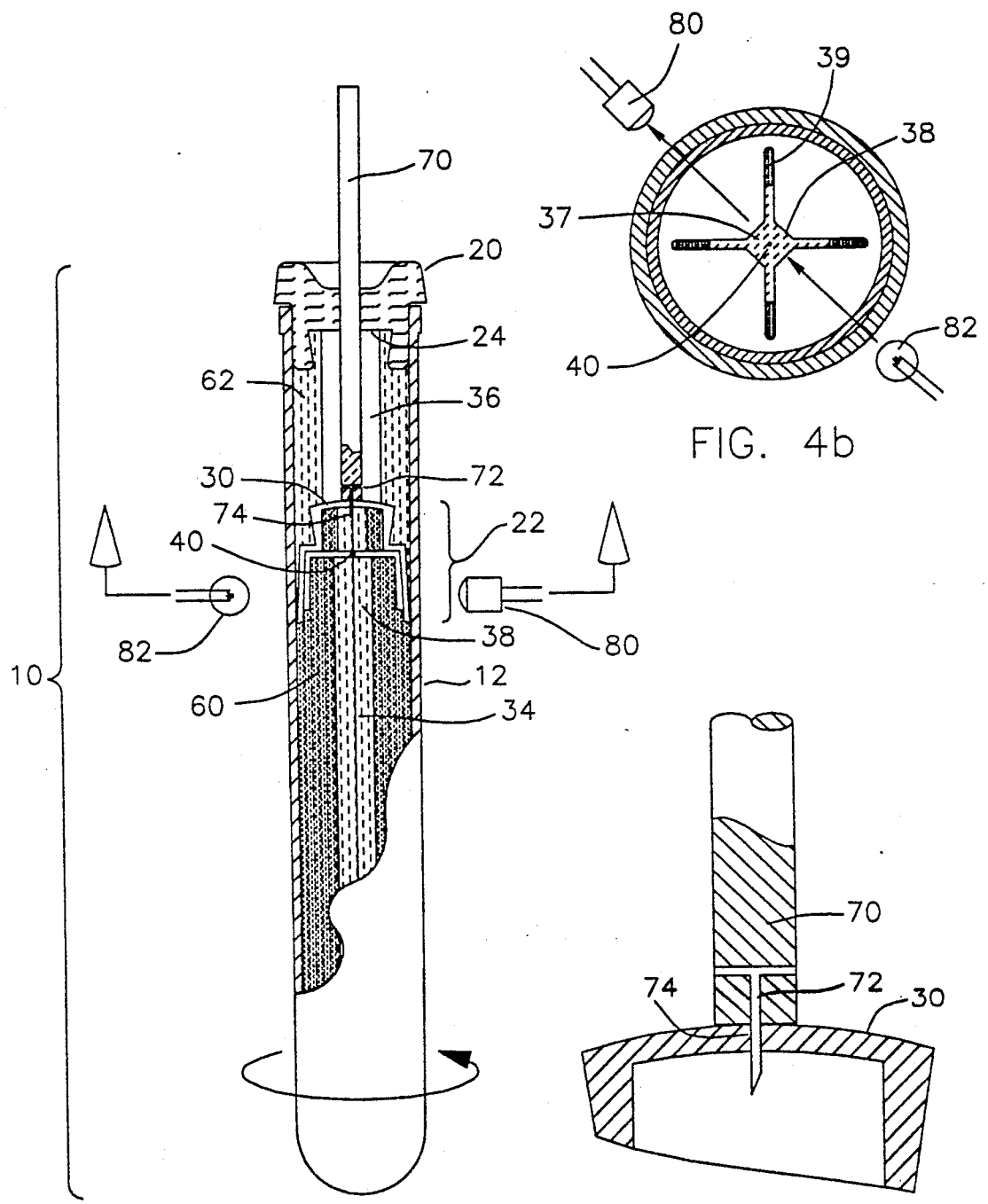

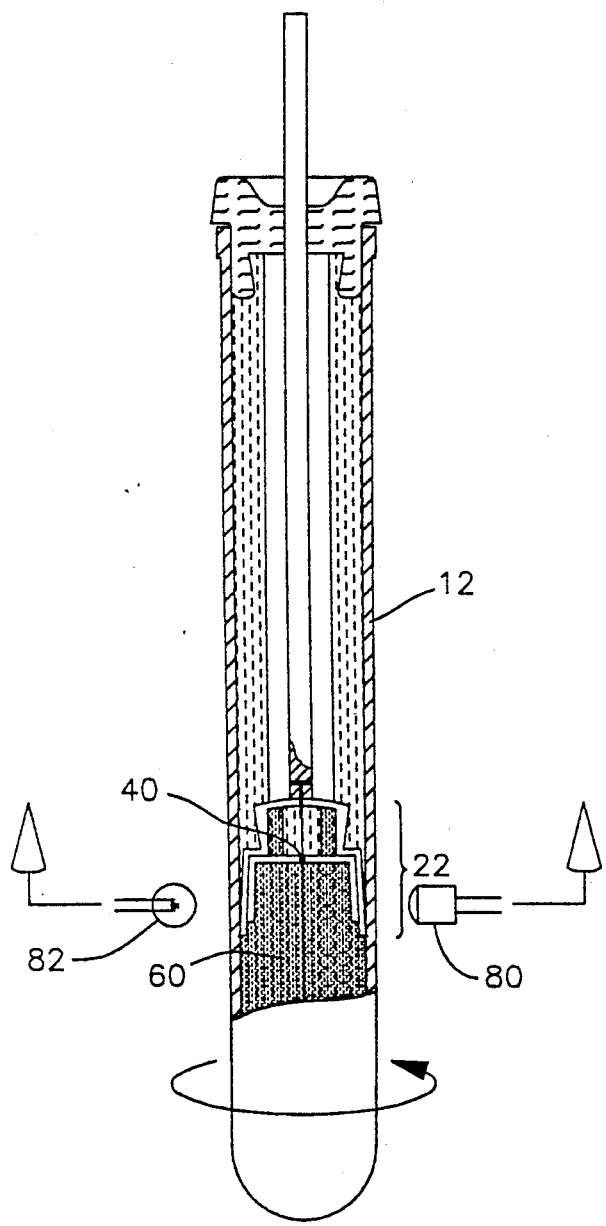
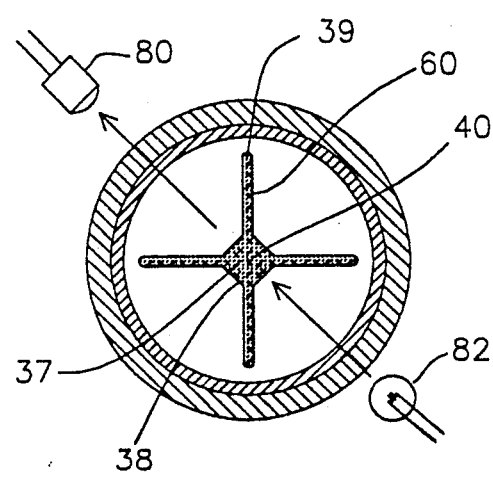
FIG. 5a
FIG. 5b

APPARATUS FOR SEPARATING PHASES OF BLOOD

REFERENCE TO RELATED APPLICATION

This is a continuation-in-part of U.S. patent application Ser. No. 07/192,847 filed May 11, 1988, now abandoned, which was a continuation of U.S. patent application Ser. No. 07/033,769 filed Apr. 3, 1987, now U.S. Pat. No. 4,828,716.

FIELD OF THE INVENTION

The present invention refers to a method and apparatus for separating a pre-selected phase of a sample of liquid such as blood contained in a chamber, and pertains to means for ordering the phases of a sample of liquid contained in a chamber by rotating the chamber about its longitudinal axis. In particular, the invention pertains to apparatus for collecting a blood sample in a tubular chamber, separating the phases of the blood sample by rotating the tubular chamber about its longitudinal axis, and receiving from the chamber the separated phases in order of phase.

BACKGROUND OF THE INVENTION

Blood to be analyzed for diagnostic and monitoring purposes is customarily collected by venipuncture through a special cannula or needle attached to a syringe or evacuated collection tube. Such collection techniques and devices must offer ease and flexibility of use because of the large number of blood specimens that are processed and because of requirements for additives, variable volumes and adaptation to individual medical conditions.

Separation of the constituent phases, serum or plasma from the cells, is often necessary for laboratory analysis and is usually carried out by centrifugation or, occasionally, by filtration. This separation may require fractionation of minor as well as major components. Once separated the phases are best kept in an inert container, physically and chemically isolated, to avoid disturbance of analyte concentrations. It may be necessary to store them under controlled environmental conditions of temperature, atmosphere or light.

The blood and its fractions have characteristics of volume, color and turbidity, of which it is important the analyst take note, since these may affect subsequent analyses. The blood may contain infectious agents and should be kept isolated, preferably in a closed system to reduce exposure to laboratory personnel. Blood specimens may be processed either in small numbers in physicians' offices where compactness and simplicity of use are required or in large numbers in clinics and hospitals where efficiency and assured identification are essential and automation is desirable.

Thus there is a need for a blood collection and separation device or system which combines the features of: ability to separate the blood phases under conditions which limit personnel exposure; maintenance of these phases separated and unchanged; monitoring of gross characteristics of the phases; ready adaptability to varying blood collection requirements; and flexibility for stand-alone use or integration into automated systems.

Serum and plasma are commonly used analytical samples. If serum is desired the specimen must be permitted to clot or coagulate before further separation is attempted. Activation of this clot formation may result as a consequence of contact with the glass collection tube in which the blood was collected and can be enhanced by the addition of various clot-activating materials as described in Zine U.S. Pat. No. 4,189,382. If plasma is desired the specimen must have an anticoagulant mixed with it immediately after collection. For this purpose such anticoagulant materials are commonly placed in blood collection devices at the time of manufacture.

The most commonly used blood collection devices are evacuated tubes. They are characterized by advantages and disadvantages in certain situations. The pre-evacuated blood collection tube (such as described by Kleiner U.S. Pat. No. 2,460,641) has the following advantages: once sterilized, its interior remains sterile without additional packaging; simplicity of structure and use, in that its basic form consists of only a glass tube permanently closed at one end with a rubber stopper in the open end; and it is self-sealing when blood drawing is complete and the cannula which was used to puncture the rubber stopper has been removed.

The blood plasma or serum phase is readily separated from the blood cells or clot phase by centrifugation since the specific gravities of these two phases are different. The recommended and usual practice is to centrifuge the specimen at a relative centripetal acceleration of 1,000 to 1,200 gravities for about 10 minutes. Various materials and devices have been described to physically separate the serum or plasma from the cellular phase, which are either activated during centrifugation or applied after separation is complete. These include gel-like compositions with densities intermediate to the phases as described, for example, in Kessler U.S. Pat. No. 4,350,593 and Zine U.S. Pat. No. 3,852,194 and 4,083,784. Such substances, as commonly used, are sealed in the evacuated blood collection tube at the time of manufacture and will migrate to, and form a barrier at, the interface between the blood phases under the influence of the correct centrifugal force. A problem with such materials is that although they are made from substances with low chemical reactivity they nevertheless contain substances which will contaminate the serum or plasma (such as low levels of some metals used as catalysts for the formation of those compositions). Some substances which are determined by blood analysis (such as low concentrations of organic-soluble, hydrophobic drugs) can be significantly adsorbed or absorbed out of the sample by such gel-like materials, resulting in incorrect analyses. Other separators consisting of a variety of plug-like objects have been used as described, for example, in Villa-Real U.S. Pat. No. 4,492,634, Coleman U.S. Pat. No. 3,508,653, Nugent U.S. Pat. No. 4,417,981, Cornell U.S. Pat. No. 4,425,235, and White U.S. Pat. No. 4,369,117. Unfortunately, these devices are more expensive to make and insert into the pre-evacuated collection tube and the barriers they provide are no more reliable or effective than the simpler, less expensive gel-like separation materials.

Irrespective of the relative expense of plug-like barrier devices, the main problem with such barriers of the prior art is that during blood collection it is impossible to keep blood from getting between the tube closure and the barrier device. Coleman, U.S. Pat. No. 3,508,653 describes a plug-like barrier which is removably attached to the stopper, but does not demonstrate how blood is prevented from being interposed between the stopper and plug-like barrier. In fact, he states that the plug need not be attached to the stopper, but only restrained from moving prior to centrifugation. Since Coleman's barrier must allow passage of fluid around it when pressure is applied, it follows that the space between the barrier and stopper, along with the rest of the tube, is evacuated prior to blood collection. If the space between the stopper and barrier is evacuated, then blood may forcibly fill the space between the two parts. This is entirely unacceptable because there is no certain way of isolating the cellular blood component of the blood located between the barrier and the stopper from the separated serum or plasma thus negating the effect of the barrier. Both Nugent U.S. Pat. No. 4,417,981 and Adler U.S. Pat. No. 3,929,646 try to address this problem by providing a path for the whole blood to move around and past the plug-like barrier during sample collection or centrifugation. However, in practice once blood interposed between the stopper and barrier has clotted, these passages are insufficient to ensure that the cellular component of the interposed blood will migrate to the other side of the barrier during centrifugation. Both Nugent and Cornell U.S. Pat. No. 4,425,235 try to address this problem by including a migrating gel in their plug-like barriers, but this negates the benefits of solid barriers over gel barriers. White, U.S. Pat. No. 4,369,117, avoids the problem by inserting his plug-like barrier into the collection tube after blood collection has occurred. This is not desirable because an additional, hazardous step is required in handling an open tube.

An additional problem with many barriers is incomplete isolation of the serum or plasma from the cellular phase. In the case of gel-like barriers, severe jarring as might occur if the sample is shipped or mailed to a testing laboratory, may disrupt the seal provided by the barrier. If the isolation provided by the barrier is incomplete or disrupted, interaction of the separated phases will cause inaccurate analytical results. Moreover, prolonged contact of the blood phases with a gel-like barrier separator will increase the degree of analytical error caused by interaction between the blood and the barrier. Therefore, with most such devices it is necessary to separate the phases soon after the blood is collected and then transfer the separated plasma or serum to another container for prolonged storage or transport. Problems which then arise are that the transferred sample can become incorrectly identified and that the process of transfer exposes the user to potentially hazardous or infectious blood.

A portion of the serum or plasma may be completely isolated after centrifugation by a device which is inserted into the open end of the collection tube and permits the one-way flow of serum from the collection tube into a separate sampling container through a filter which prevents any of the fibrin from passing into the serum or plasma sample. Fibrin in blood serum can cause blood analysis machines to clog; therefore, many clinical chemistry laboratories filter all serum as a precaution. Such filtering devices are described, for example, in Dojki U.S. Pat. No. 4,464,254, Adler U.S. Pat. No. 3,929,646, Cassaday U.S. Pat. No. 4,602,995 and are manufactured and distributed under the name of "serum/plasma filter" by W. Sarstedt, Inc. It is possible to isolate the phases of blood with such a device so as to prevent diffusion of ions or other interaction between the phases. However, their use requires additional manipulation of the collection tube, consequent exposure of the user to the blood specimen and risk of contamination of the sample. Related devices employ multiple flexible containers with provision for flow of blood fractions from the collecting blood bag into a separate reservoir (for example, Eberle U.S. Pat. No. 4,447,220 and Persidsky U.S. Pat. No. 4,322,298) but these are bulky complex systems only for the separation of anticoagulated blood and are not suitable for collection and preparation of samples for routine clinical analysis.

For most analysis of centrifuged blood samples it is necessary to dispense a portion of the sample to other containers such as analyzer sample cups. Presently, this is done a number of ways. The most common method is to remove the stopper and use a dropper pipette to transfer some of the sample from the open tube to the alternate container. This procedure is hazardous in that removal of the stopper may generate aerosols containing infectious agents, and handling an open sample tube introduces a danger of spilling the sample. Another popular method of dispensing a sample to additional containers is to remove the stopper and simply decant into the additional containers. This method is even more hazardous than the first because skill is required to decant a small amount of serum or plasma without spillage.

Some devices have been made which attempt to address these hazards. One such device is the Tip-Top TM Dispenser Cap made by Helena Laboratories of Beaumont, Tex. The Tip Top dispenser is fastened to the open end of a centrifuged blood collection tube, inverted, and then squeezed causing a portion of the sample to be dispensed through an orifice to a sample cup. The primary difficulty with the Tip Top dispenser and others like it is that it still requires the hazardous step of removing the stopper of the blood collection tube. A device which does not require stopper removal for dispensing a blood sample is the CleanTech TM system made by Clean Tech SCI AG of Langenthal Switzerland. The CleanTech system consists of several components including a cannula to puncture the stopper, a machine to insert the cannula into the stopper, a pipette to access the sample through the stopper and a pump which fastens to the pipette to draw the sample from the tube. This device goes far to address the hazards of dispensing a sample, but it is a relatively complex device and requires several steps to use.

In some situations the use of conventional centrifuges to separate serum or plasma from the cellular component of blood specimens is undesirable because it requires a large and expensive centrifuge, best suited for separating batches of several specimens simultaneously. This operation is inefficient when the serial analyses of single samples is urgently required. Time must also be taken to properly balance the centrifuge rotor to prevent excessive vibration which may damage the machine and specimens. An apparatus such as the "Stat-Spin" axial centrifuge, developed and manufactured by Norfolk Scientific, Inc. (Norwood, Mass.), can effect this separation on a single specimen more quickly, however, the technique employed by this apparatus is limited to anticoagulated blood, collected separately in a conventional blood collection device and transferred to a specialized centrifuge chamber containing gel-like separation material. Moreover this transfer increases the hazard of contamination or loss of the sample, misidentification, and exposure of the operator to potentially infectious material in the blood. The use of an additional container increases the cost of analyzing a sample.

Similar objections and disadvantages apply to the "ACR-90" centrifuge chamber, rotor and "Airfuge" drive manufactured and sold by Spinco Division of Beckman Instruments, Inc. (Palo Alto, Calif.). This rotor is dual chambered and intended for isolation of the large lipid particles from lipemic sera. At high rotational speeds (typically greater than 90,000 rpm) the plastic chamber deforms, permitting the less dense lipid phase to migrate to a second chamber where it is trapped. Other axially spun centrifuge rotors, with a single volume often divided by vanes, are well known as "zonal rotors" and used for harvesting particles from a large volume (0.3-1.7 liters) of dilute solution such as preparations for vaccine by virologists and other such macromolecular isolates (Anderson, N.G.: Preparative zonal centrifugation Methods of Biochemical Analysis 1967; 15: 271-310). Zonal rotors may be loaded and unloaded through a rotating seal while spinning (dynamically). A majority cannot be loaded or unloaded statically, while a few cannot be loaded or unloaded dynamically. In either case they are usually used for ultracentrifugation at rotational speeds of 20,000-60,000 rpm. Fluids are loaded by a pump and unloaded from them by displacement with air or a denser fluid pumped in during rotation. A single chamber, axially spun, centrifuge rotor with a variable volume which can be used for separation of plasma from blood was described by Brown in U.S. Pat. No. 4,530,691. This is intended for preparation of blood fractions for therapeutic use and relies upon the fractionation by centrifugation and isolation of those fractions by release of pressure exerted by a spring-loaded movable mandrel upon a flexible chamber. In this way the higher density cellular components can be taken off from the outer radius and the plasma through the center through fluid conduits while the rotor is in motion. Neither of these technologies (zonal ultracentrifugation nor centrifuge with a movable mandrel) is suitable for the fractionation of blood specimens as normally required for clinical analyses. The volumes are too large; they require the use of anti-coagulants and cannot be used with clotted whole blood; and they are not readily adapted for automated procedures.

Procedures for blood separation and analysis expose laboratory personnel to infectious agents that may be passed through contact with blood; e.g. hepatitis or acquired immune deficiency syndrome. In addition, conventional batch processing of blood specimen separation is labor-intensive and has not generally been automated whereas other processes in clinical laboratories have. Automation of blood separation can effectively isolate laboratory personnel from the dangers of blood processing while theoretically increasing the speed of the overall analytical procedure.

McEwen et al U.S. patent applications Ser. No. 07/033,769 and Ser. No. 07/192,847 describe a method of separating a sample of blood contained in a tubular chamber wherein the tubular chamber and its contents are rotated about the chamber's longitudinal axis and providing a means of processing a sample of blood having the features of: ability to separate the blood phases under conditions which limit personnel exposure; maintenance of these phases separated and unchanged; monitoring of gross characteristics of the phases; ready adaptability to varying blood collection requirements; and flexibility for stand-alone use or integration into automated systems. The present invention provides an improved blood collection and separation device and provides for including an apparatus to dispense a portion of the separated blood sample separated in the blood collection and separation device according to the invention of McEwen et al as described in U.S. patent applications Ser. No. 07/033,769 and Ser. No. 07/192,847. U.S. patent applications Ser. No. 07/033,769 and Ser. No. 07/192,847 are herein incorporated by reference.

SUMMARY OF THE INVENTION

The present invention provides an apparatus for partitioning a pre-selected phase of a liquid such as blood comprising: a tubular chamber having a pre-determined initial length and a cross sectional shape which is substantially constant along its length, in which a sample of liquid is contained; a sample ordering means in which the tubular chamber is rotated about its longitudinal axis to order the phases of the sample; and, a sample partitioning means for determining the portion of the sample to be partitioned.

Other objects of the present invention include: providing a sample indication means for indicating a parameter of the sample and producing a signal representative thereof; providing sample partitioning means which incorporates sample indication means by way of construction from substantially translucent material; and, providing a light source, a light detector and sample partitioning means formed to preferentially guide light from said light source to said light detector.

A further object of the present invention provides for an apparatus for partitioning a pre-selected phase of a liquid such as blood comprising: a tubular chamber having a pre-determined initial length and a cross sectional shape which is substantially constant along its length, in which a sample of liquid is contained; a sample ordering means in which the tubular chamber is rotated about its longitudinal axis to order the phases of the sample; a closure means disposed to seal said tubular chamber; and, a sample partitioning means for determining the portion of the sample to be partitioned where said sample partitioning means may be removably connected to said closure means and is formed so as to prevent the interposition of fluid between itself and said closure means when the two are connected.

The present invention consists of: an apparatus comprising an evacuated, tubular chamber, blood collection device, which can be used in a conventional manner with available blood collection cannulae to collect a blood sample, and contains clot activation materials, chemical additives, or anticoagulants as required; a separating means consisting of a device to rotate the tubular chamber about its own longitudinal axis; and, a means for displacing a partition within the tubular chamber while the tubular chamber is being rotated such that the separated phases of the blood sample are displaced into a containment sub-volume within the tubular chamber in order of increasing density.

Further, the invention provides indication as to the phase of the sample that is displaced into the containment sub-volume. The invention also provides a closure means for sealing the tubular chamber and a connection means for connecting the closure means to the separation means such that fluid cannot be disposed between the two when they are connected.

Advantageously, the invention provides a physical barrier between the phases of the sample, such that the separation of the phases can be maintained over a long time period. Also, it is possible to use the blood collection and separation apparatus of the present invention in a conventional centrifuge.

The present invention also provides an apparatus for safely dispensing a sample of liquid such as blood serum from a closed blood collection device whereby the apparatus is fastened to the blood collection device and has access to the interior of the device through a hole created in its closure. The apparatus comprises a flexible conical bulb, through which the sample passes as it is being dispensed; a dispensing tip having an orifice of an appropriate size to prevent spillage but allow flow of the sample when the conical bulb is squeezed; a hollow spike which penetrates the closure of the sample collection device and conducts the sample from the collection device into the conical bulb for dispensing.

BRIEF DESCRIPTION OF DRAWINGS

FIG. 4a shows the partitioning of the blood sample inside the blood collection and separation apparatus.

FIG. 4b is an axial cross-section of the blood collection and separation apparatus through the separator assembly while the blood sample is being partitioned.

FIG. 4c is an enlarged cross-sectional view of the probe tip and separator assembly.

FIG. 5a shows the cellular component of the blood sample inside the blood collection and separation apparatus filling the separator assembly and blocking the optical path across the separator assembly.

FIG. 5b is an axial cross-section of the blood collection and separation apparatus through the separator assembly with the cellular component of the blood sample filling the separator assembly.

DESCRIPTION OF SPECIFIC EMBODIMENTS

Figure 1C:
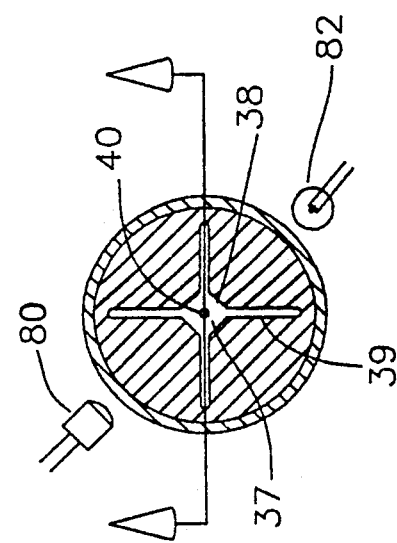
FIG. 1c is an axial cross-section of the blood collection and separation apparatus through the separator assembly.

Referring now to the drawings in detail, FIGS. 1 through 7 illustrate the preferred embodiment of a sample collection and separation apparatus of the present invention.

Figure 1B:
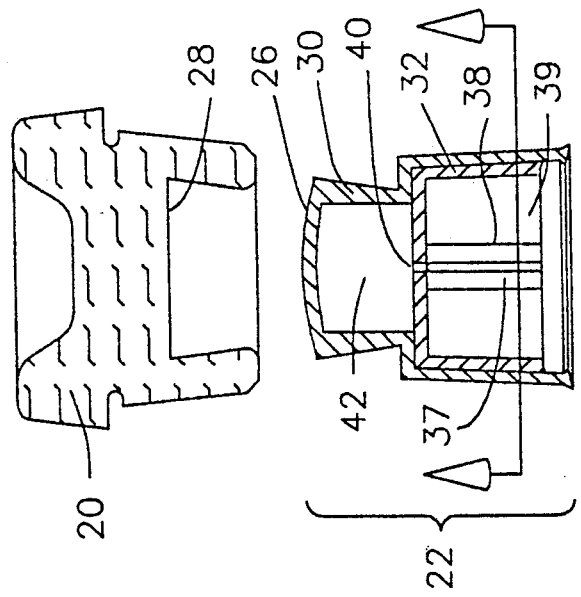
FIG. 1b is an enlarged view of the cap and separator assemblies of the blood collection and separation apparatus.
Figure 1A:
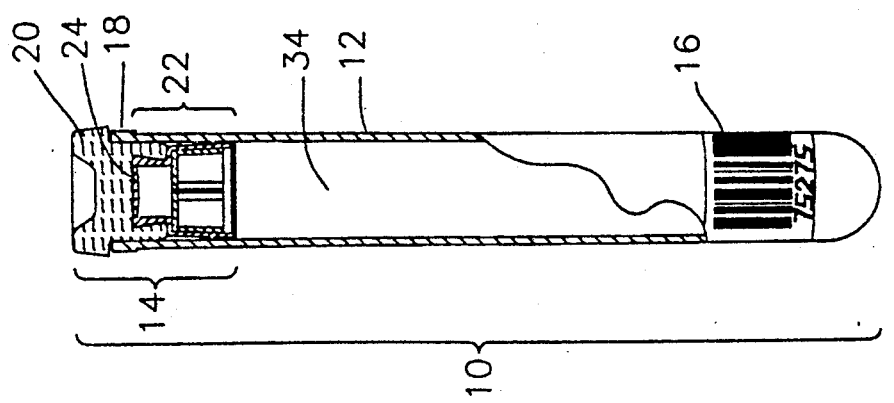
FIG. 1a shows the blood collection and separation apparatus of this application.

The preferred sample collection and separation apparatus 10 shown in FIGS. 1a through 1c consists of a tubular chamber 12 and formed cap assembly 14.

Tubular chamber 12 is preferably constructed of glass, plastic or some other transparent or translucent and chemically inert material, or combination of such materials, has predetermined length and constant cross-sectional shape, and has a closed end and an open end shaped to receive and be adequately sealed by cap assembly 14. Tubular chamber 12 may also include non-removable machine readable markings 16, such as a bar code, located around the perimeter of said tubular chamber 12. Said markings allow a specific sample collection and separation apparatus 10 to be uniquely identified while it is being rotated around its longitudinal axis. Said markings 16 may be attached to the exterior of tubular chamber 12, or may be located between layers forming the walls of tubular chamber 12 thereby being embedded inside said tubular chamber. Tubular chamber 12 may also be formed to incorporate fastening lip 18. In the preferred embodiment, fastening lip 18 is formed into tubular chamber 12 around the circumference of the open end of said tubular chamber and permits the fluid dispensing apparatus of this invention to be securely fastened to the preferred embodiment by being pressed over said fastening lip.

Cap assembly 14 comprises piercable closure segment 20 and separator assembly 22 attached at separable joint 24. Cap assembly 14 is constructed to allow detachment of separator assembly 22 from closure segment 20 at separable joint 24 when probe 70 of FIG. 4a is forced through said closure segment 20. Closure segment 20 and separator assembly 22 have interconnecting surfaces shaped so that separator assembly 22 is interlocked with the closure segment 20 and is prevented from becoming detached from closure segment 20 prior to the action of said probe. The interlock created by the interlocking surfaces has sufficient strength to allow a sample contained within sample collection and separation apparatus 10 to be separated by conventional centrifugation. In the preferred embodiment, said interconnecting surfaces are bevelled so as to interlock. Separator assembly 22 is formed with convex surface 26 and closure segment 20 is formed with corresponding flat surface 28. When said separator assembly and said closure segment are connected convex surface 26 presses against flat surface 28 so as to provide a pressurized seal between separator assembly 22 and closure segment 20 that is adequate to prevent blood from becoming interposed between the closure segment 20 and the separator assembly 22 during blood collection. Although a bevel shape is used in this embodiment to provide a separable joint, other means such as adhesives applied so as to provide a sealed interface could also be used. As such, the use of a bevel-shaped interlock is not meant to be a limitation of this patent.

Said closure segment 20 is preferably constructed of a self-healing, medical grade, brominated butyl rubber. Closure segment 20 forms a seal with the inside wall of tubular chamber 12 adequate to allow said tubular chamber to be pre-evacuated to aid in blood sample collection.

Separator assembly 22 is comprised of sealing element 30 and insert 32. Sealing element 30 is formed so as to provide a fluid-tight seal between itself and insert 32 and a similar seal with tubular chamber 12. Both seals are adequate to prevent blood cells from passing from the blood sample collection chamber 34 (of FIG. 4a) around separator assembly 22 into serum collection chamber 36 (also of FIG. 4a) when said separator assembly 22 is displaced. Formed into insert 32 is a passage 38 having an X-shaped cross section open at one end to blood sample collection chamber 34 and closed at the other end except for flow restriction 40 which allows fluid to flow irrespective of whether the tube is moving or stationary into intermediate volume 42 but not into the serum collection chamber 36. Passage 38 comprises an axially central part 37 extending substantially along the longitudinal axis of the tubular chamber 12. Four slots 39, equally spaced about the axis of the passage 38, are contiguous with and extend radially outward from the central part 37 of the passage 38. Intermediate volume 42 is a volume defined by the interior top surface of sealing element 30 and the exterior top surface of insert 32, which serves two purposes: firstly, said intermediate volume permits blood to be drawn into blood sample collection chamber 34 without the necessity of having a blood drawing needle pierce sealing element 30 precisely on the central axis; and secondly, as fluid passes through passage 38 during axial separation, intermediate volume 42 acts as a second centrifuge chamber trapping heavier components of the fluid, such as blood cells, before they pass into serum collection chamber 36. Both sealing element 30 and insert 32 are substantially transparent and preferably made of a thermoplastic material such as DuPont's Elvax 150 TM. In practice, sealing element 30 may be created by insert molding said sealing element into closure segment 20 which has been formed prior to the insert molding operation. Advantageously, DuPont's Elvax 150 TM has adhesive properties which cause sealing element 30 to bond with closure segment 20 during the insert molding operation.

Figure 2:
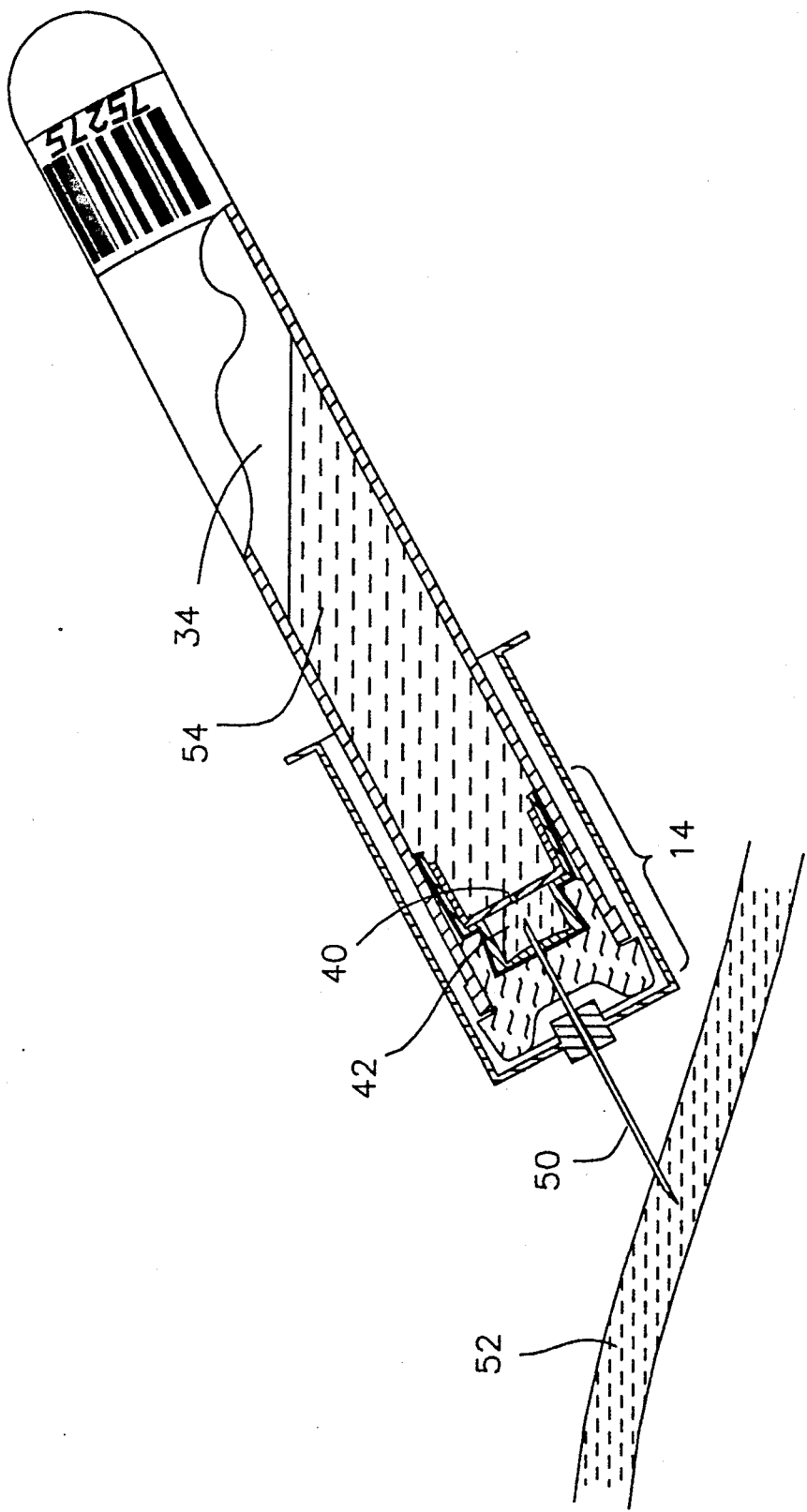
FIG. 2 shows the blood collection and separation apparatus of this invention being used to draw a blood sample from a blood vessel.

As shown in FIG. 2, when blood drawing needle 50, one end of which is inserted in a patient's blood vessel 52, punctures cap assembly 14, blood sample 54 will be drawn by a pre-established vacuum into blood sample collection chamber 34 by way of intermediate volume 42 and flow restriction 40. Removal of blood drawing needle 50 allows the hole created in cap assembly 14 by blood drawing needle 50 to substantially re-seal.

Figure 3:
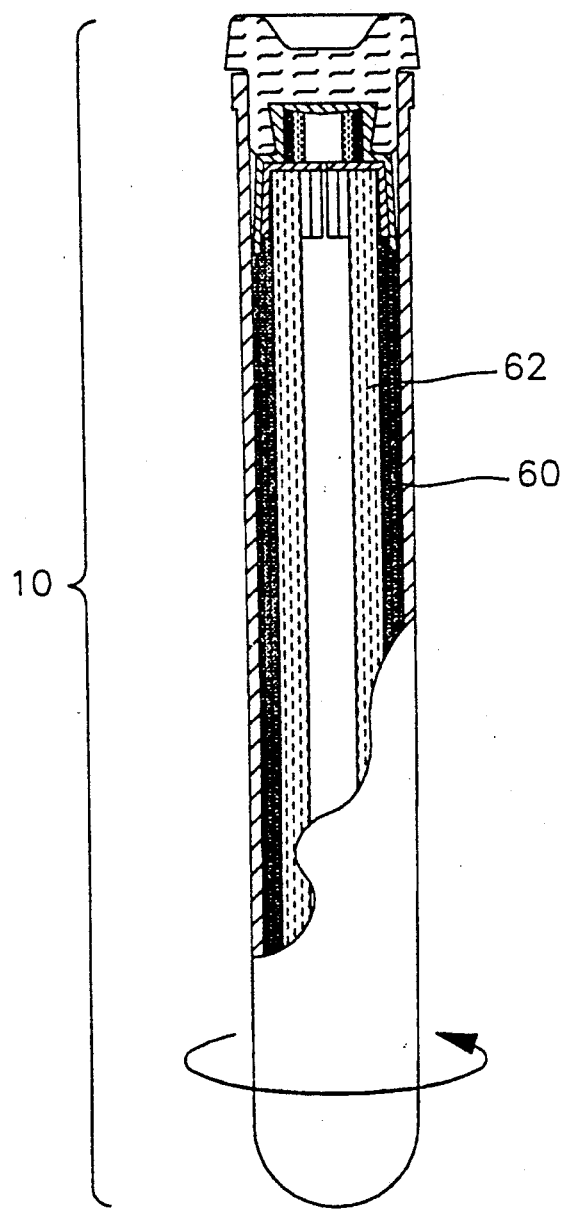
FIG. 3 shows the blood collection and separation apparatus being spun around its longitudinal axis so as to cause separation of the blood sample into its denser cellular component and less dense, non-cellular component.

FIG. 3 shows sample collection and separation apparatus 10 being spun around its longitudinal axis so that concentric ordering of blood into cellular component 60 and non-cellular component 62 occurs.

FIGS. 4a and 4b illustrate the separation process where probe 70 is inserted through piercable closure segment 20. Said closure segment 20 forms a seal around said probe 70 so that sample collection and separation apparatus 10 remains hermetically sealed. Probe 70 rotates with sample collection and separation apparatus 10, and acts as a link to transmit an axial force to separator assembly 22. This force causes separator assembly 22 to detach from closure segment 20 along separable joint 24 and be displaced along the length of tubular chamber 12. This displacement decreases the volume of blood sample collection chamber 34 and increases the volume of serum collection chamber 36 which is created when separator assembly 22 is disconnected from closure segment 20.

As separator assembly 22 is displaced axially along tubular chamber 12 by probe 70, cannula-like conduit 72 at the tip of probe 70 punctures sealing element 30 creating port 74. Cannula-like conduit 72 allows fluid located near the longitudinal axis of tubular chamber 12 to pass from blood sample collection chamber 34 through passage 38 and flow restriction 40 into intermediate volume 42, and then through cannula-like conduit 72 to serum collection chamber 36. Air is the first fluid to pass from blood sample collection chamber 34 to serum collection chamber 36 but as the volume of said blood sample collection chamber is decreased, non-cellular component 62 also enters said serum collection chamber. As separator assembly 22 is moved further along tubular chamber 12, cellular component 60 begins to enter passage 38. The construction of the passage 38 is such that centrifugal force causes the cellular component 60 that enters passage 38 to gradually fill the slots 39 from the radially outermost ends of the slots 39 inward to the central part 37 of the passage 38. As the cellular component 60 moves into the slots 39, the optical path along which the light from source 82 propagates to reach sensor 80 becomes increasingly smaller in cross section because of the light-obstructing effect of the cellular component 60. Further, because the cellular component moves radially inward through the slots, the light from the sensor is ultimately constrained to pass substantially completely through the central part 37 of the passage 38. The light then re-enters and passes through insert 32 and is received by optical sensor 80. The result of the constraint described above is that light reaching optical sensor 80 is indicative of the optical parameters of said blood sample in the central part 37 of passage 38. More particularly, because the light from source 82 is constrained to pass through the central part 37 of the passage 38, any subsequent obstruction of the light passing through the central part 37 (as would occur when cellular component 60 enters the central part 37 just prior to moving toward the serum collection chamber 36) will cause a substantial change in the magnitude of the output of sensor 80. Such a substantial change in the sensor output provides a precise indication of, for example, when to halt the separation process to thereby prevent cellular component 60 from entering the serum collection chamber 36.

As shown in FIGS. 5a and 5b, when cellular component 60 enters the central part 37 of passage 38, it obstructs the light. This obstruction is then detected by optical sensor 80 signifying completion of sample separation. As previously described, if a small portion of cellular component 60 should happen to move through flow restriction 40 without detection by optical sensor 80, it passes into intermediate volume 42 where centrifugal force causes it to move off axis and become trapped against the periphery of said intermediate volume.

Figure 6:
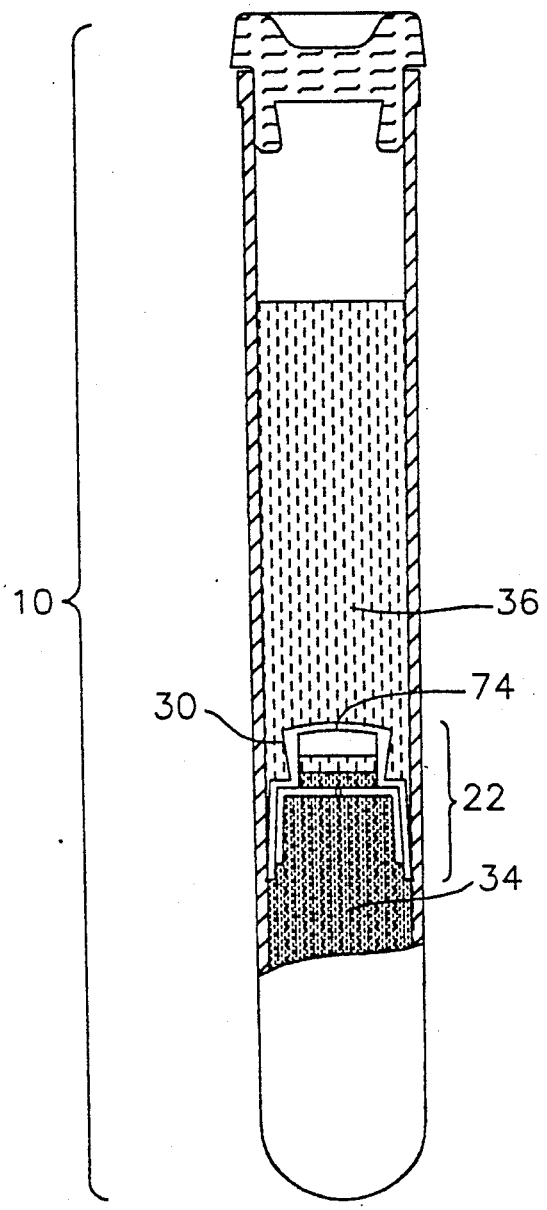
FIG. 6 shows the blood collection and separation apparatus after completion of axial processing with the cellular and non-cellular components of the blood sample partitioned within the apparatus.

FIG. 6 illustrates collection and separation apparatus 10 after displacement of said separator assembly 22, and rotation of blood collection and separation assembly 10 has been stopped. Removal of cannula-like conduit 72 from sealing element 30 allows port 74 to close and effectively isolates the fluid in blood sample collection chamber 34 from the fluid in serum collection chamber 36.

Although in this implementation an optical method is used to detect when the interface between blood cells and serum is reached, it is clear there are a number of other criteria (i.e. differences in viscosity, density or magnetic properties) that could be used instead. Similarly, although in this preferred embodiment a passage 38 is used to direct light through the central part 37 of the separator assembly, it is clear that there are other, similar means of providing this function. For example, forming radial arms of an opaque material into a transparent separator would direct light in manner analogous to the X-shaped passage 38 of the current embodiment.

In addition to providing a fluid path, the small diameter of the orifice of cannula-like conduit 72 provides an effective method of filtering fibrin from separated serum passing into serum collection chamber 36. Blood collection and separation assembly 10 allows both serum from cell and fibrin from serum separation to be accomplished with one operation.

Figure 7:
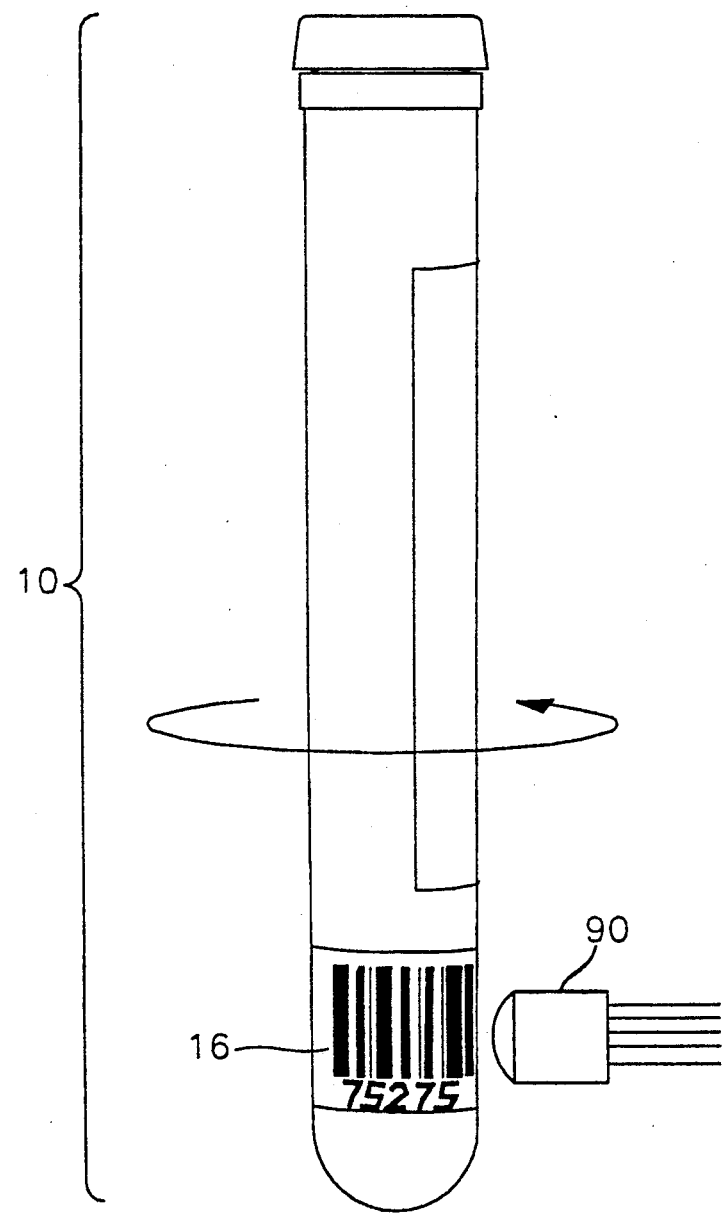
FIG. 7 shows the embedded identification attached to the blood collection and separation apparatus being rotated in front of an optical sensor.

FIG. 7 snows machine readable markings 16 (in this case a bar code) attached to sample collection and separation apparatus 10 being rotated past optical identification sensor 90 (in this case a bar code reader). Advantageously, an apparatus which can accomplish separation of blood as herein described must rotate said blood collection and separation apparatus as shown and therefore can be used to identify the sample.

Figure 8C:
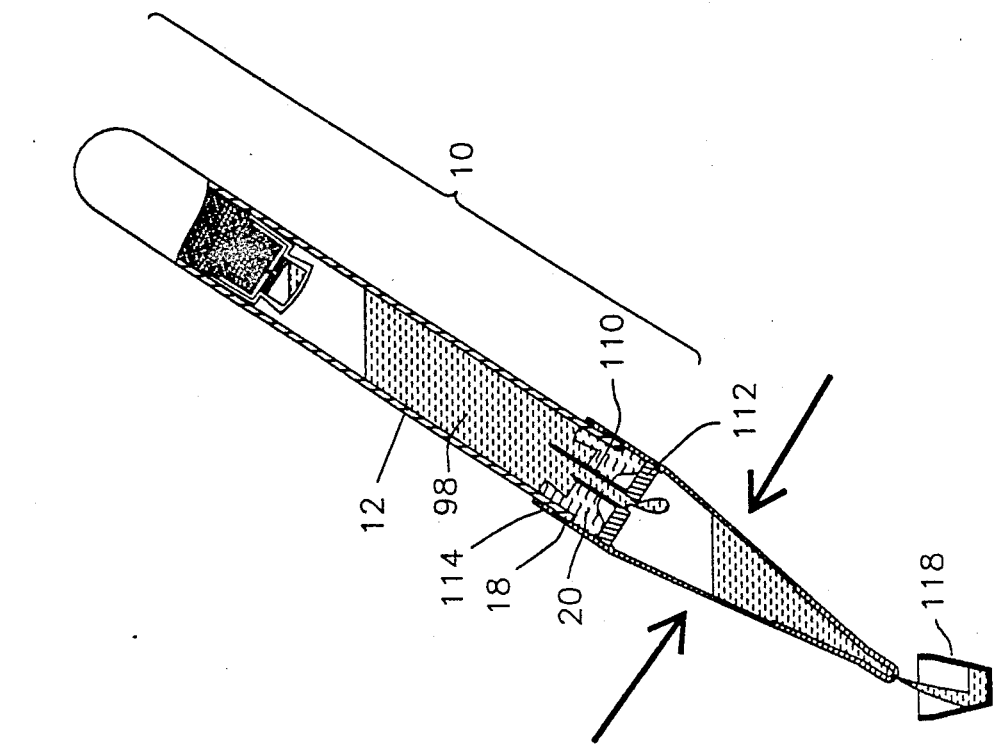
FIG. 8c shows the combined liquid dispensing and blood collection and separation apparatus being used to dispense a separated blood sample.
Figure 8B:
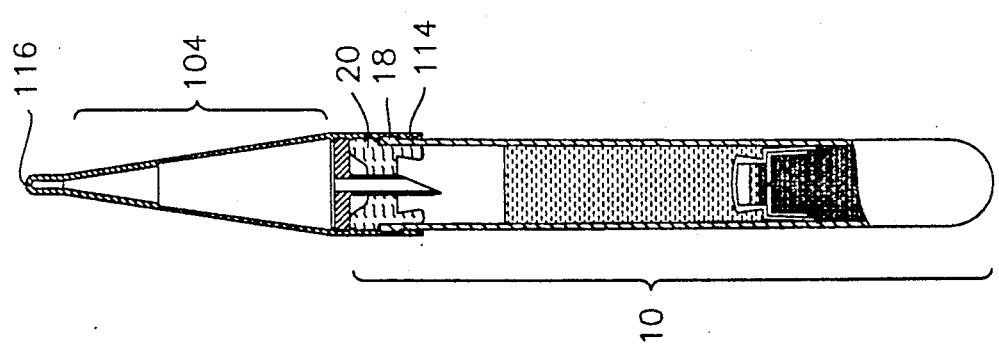
FIG. 8b shows the liquid dispensing apparatus secured to the blood collection and separation apparatus
Figure 8A:
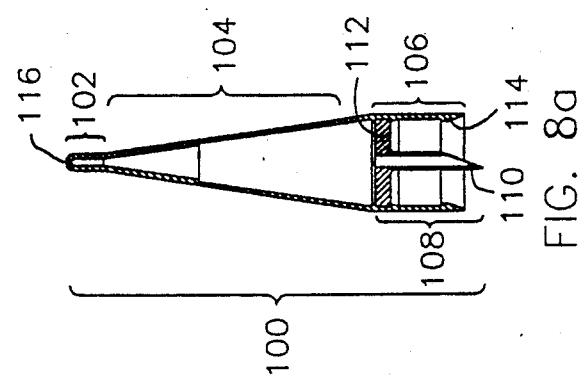
FIG. 8a shows the liquid dispensing apparatus of this application.

FIG. 8a shows the preferred embodiment of the fluid dispensing apparatus. Fluid dispensing apparatus 100 provides a means of dispensing a sample from the sample collection and separation apparatus of the present invention in such a way that removal of the stopper from said tube is not required. Fluid dispensing apparatus 100 comprises dispensing tip 102, conical bulb 104, flexible skirt 106 and pipette insert 108. Pipette insert 108 includes hollow spike 110 and solid backplate 112 and is preferably formed as one piece our of a plastic such as high-impact styrene. Referring now to FIG. 8b, hollow spike 110 allows fluid exchange between the interior of the sample collection and separation apparatus 10 and the interior of the conical bulb 104 and thereby provides a path for fluid contained in sample collection and separation apparatus 10 to enter conical bulb 104. The extreme edge of solid backplate 112 seals against the walls of conical bulb 104 so as to keep fluid contained within said bulb from leaking around solid backplate 112. Flexible skirt 106 extends past solid backplate 112 and seals against closure segment 20 and outside surface of sample collection and separation apparatus 10. Said flexible skirt incorporates latch 114 around the bottom interior circumference of said flexible skirt and, when flexible skirt 106 is pushed over closure segment 20 and fastening lip 18 formed on the exterior of sample collection and separation apparatus 10, latch 114 expands around and then engages said fastening lip 18. Dispensing tip 102 is integral to conical bulb 104 and includes orifice 116 preferably 0.38 to 0.51 millimeters in diameter which extends from the interior of conical bulb 104 to exterior of dispensing tip 102. Dispensing tip 102, conical bulb 104 and flexible skirt 106 are preferably formed as one piece out of a plastic such as polypropylene.

FIGS. 8c show the use of fluid dispensing apparatus 100 being used to dispense fluid 98 from sample collection and separation apparatus 10 into receptor 118. In use, fluid dispensing apparatus 100 is inserted onto sample collection and separation apparatus 10 after the contained sample has been separated. Hollow spike 110 is pushed through closure segment 20, so that solid backplate 112 is seated against closure segment 20 and latch 114 has engaged fastening lip 18. Once fluid dispensing apparatus 100 is attached to sample collection and separation apparatus 10, the entire assembly may be inverted and fluid contained inside tubular chamber 12 may be dispensed by repeatedly squeezing conical bulb 104. The size of orifice 116 in dispensing tip 102 is such that the fluid in sample collection and separation apparatus 10 is readily dispensed in an semi-continuous stream. The wall thickness of dispensing tip 102 is greater than that of conical bulb 104 so that dispensing tip 102 does not collapse when conical bulb 104 is squeezed.

Figure 9:
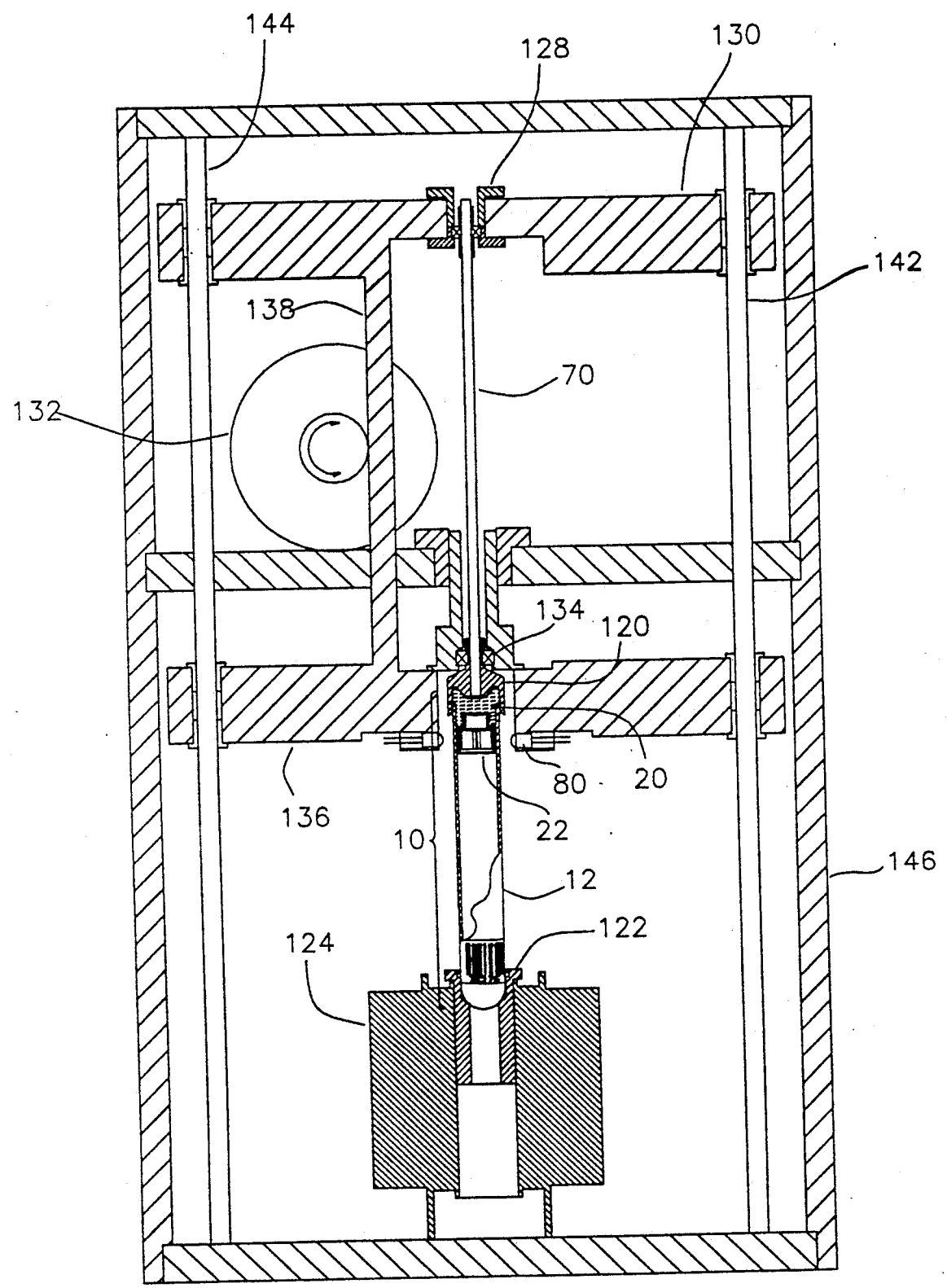
FIG. 9 shows a separating means which can be used to achieve axial separation of a blood sample contained inside the blood collection and separation apparatus of this application.

FIG. 9 illustrates a device which can accomplish blood separation as described herein of a sample contained in the preferred sample collection and separation apparatus of this invention. This device is hitherto referred to as an axial separation module.

In general, sample collection and separation apparatus 10 is clamped between restraint 120 and rotor 122 and spun at high speed by rotational motor 124. Probe 70 slides through restraint 120 yet rotates with both said restraint and said blood collection and separation apparatus. Probe 70 is axially restrained by probe bearing 128 mounted in probe block 130. Probe block 130 is moved by linear actuation motor 132, causing said probe to pierce closure segment 20, disengage separator assembly 22 from said closure segment, and displace said separator assembly along tubular chamber 12. Bearings 134 support restraint 120 and allow said restraint to spin with a minimum of frictional resistance. Sensor block 136 is connected to probe block 130 by connecting rod 138 in such a way that optical sensor 80 mounted on said sensor block is kept in alignment with separator assembly 22 while it is axially displaced by said probe. Both probe block 130 and sensor block 136 slide on alignment rods 142 and 144. Frame 146 is used to align the rotational and linear motion assemblies of the axial separation module. The small mass and low frictional resistance of rotor 122, probe 70, restraint 120, and blood collection and separation assembly 10 allow high rotational accelerations and speeds to be achieved which can dramatically reduce the time that a sample collected in blood collection and separation assembly 10 must be spun compared to a conventional centrifuge.

Figure 10:
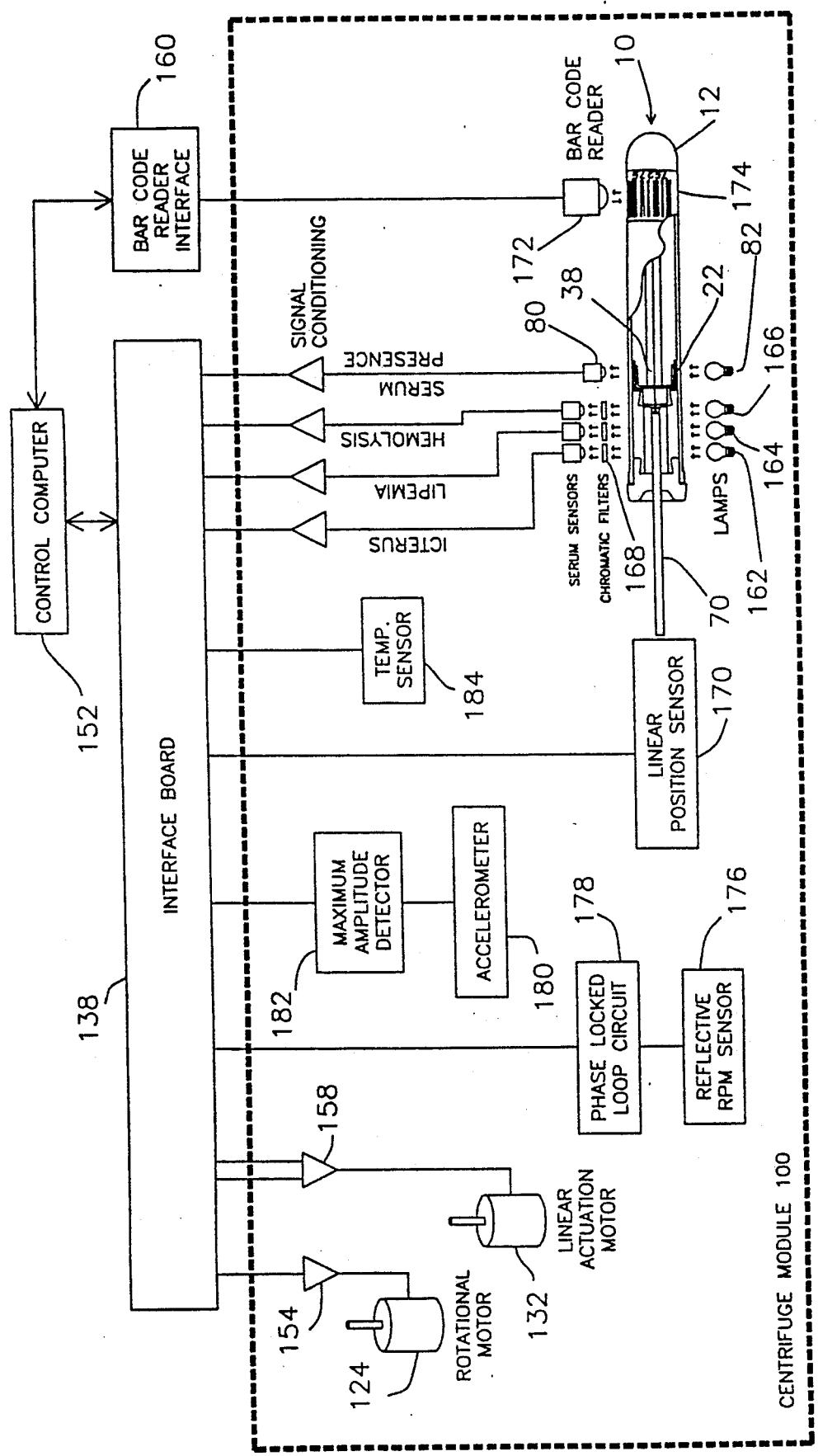
FIG. 10 shows a functional diagram of the sensing and control means that could be used to control and monitor the separating means of FIG. 9.

FIG. 10 is a schematic of the control and sensing circuit of the axial separation module. Speed control of rotational motor 124 is accomplished by control computer 152 and rotational speed control circuit 154. Control computer 152 produces a signal proportional to a set rotational speed of the tube. Rotational speed control circuit 154 causes rotational motor 124 to rotate at a speed representative of this signal.

Velocity control of the linear actuation motor 132 is accomplished by control computer 152 and linear velocity control circuit 158. Control computer 152 produces a signal proportional to a set linear velocity of the probe 70. Linear velocity control circuit 158 causes linear actuation motor 132 to advance or retract probe 70 at a speed proportional to this signal.

As FIG. 10 shows, when sample collection and separation apparatus 10 rotates, sensors mounted on the axial separation module may be used to gather information about the sample. Optical sensor 80 and light source 82, which are mechanically coupled to the movement of the probe 70 and prepositioned to be coplanar with the separator assembly 22, are used to sense the presence of cells in the center of passage 38. Three emitter and detector pairs 162, 164 and 166 use chromatic filters 168 to return a signal indicative of the color and degree of turbidity of the separated fluid as would be required to sense the presence of, for example, hemolysis, icterus, and lipemia of serum or plasma retrieved from the sample. In addition, control computer 152 may use the signals produced by optical sensor 80, and emitter and detector pairs 162, 164, and 166 to determine when optimal separation of the blood sample has occurred. Linear position sensor 170 provides an accurate measurement of the distance that the separator assembly 22 has moved within tubular chamber 12. When used in conjunction with optical sensor 80, linear position sensor 170 can help determine the volume of serum or plasma so far recovered by measuring the volume swept by separator assembly 22 from the time serum or plasma first began to enter the center of the passage 38. The identity of said sample is determined by a bar code reader 172 reading bar code 174 embedded or attached to the side of the tube as it spins. Bar code reader interface 160 transfers the read information to control computer 152. Given the tube identity input, control computer 152 could then access a general laboratory data-base to determine the test to be performed (including the volume of serum required) or to update the data-base for a patient if lipemia or excessive hemolysis are detected in the serum.

Several sensors detect conditions of the environment of the axial separation module. Reflective optical sensor 176 and phase lock loop circuit 178 use bar code 174 to produce a signal proportional to the speed of rotation of the tube. The control computer 152 uses this signal to calculate the centrifugal force produced inside the tube and thus, for a given speed of rotation, determine the minimum spin time required for adequate separation of the blood sample. Accelerometer 180 with maximum amplitude detector 182 produce a signal proportional to the maximum instantaneous vibration of the axial separation module structure to detect gross abnormalities in operation. Temperature sensor 184 is used to monitor the temperature inside the axial separation module and allows for observation of any increase in frictional heat generation.

Figure 11:
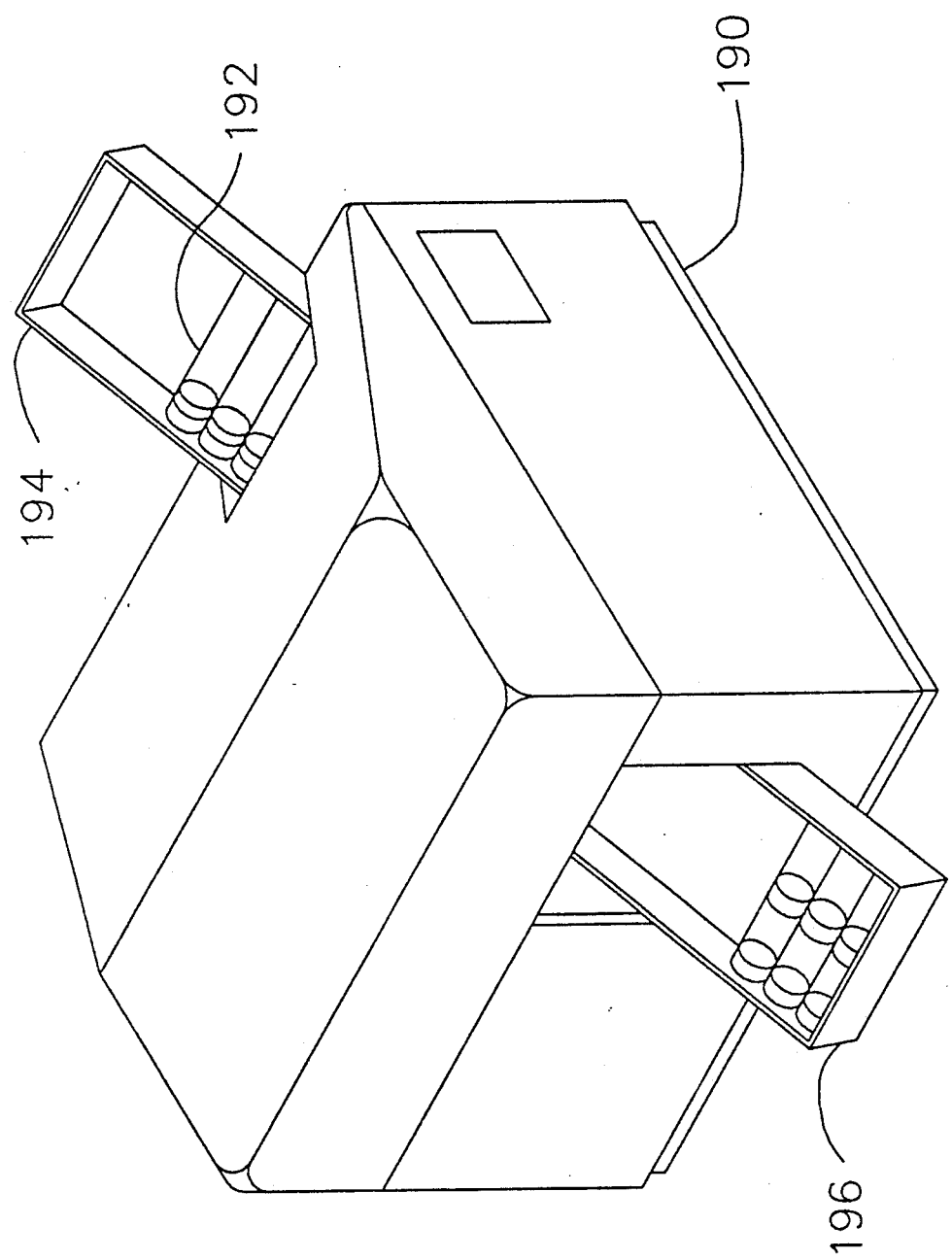
FIG. 11 shows the exterior encapsulation of the separating means of FIG. 9.

FIG. 11 is an illustration of preferred axial separation module embodiment 190 as it would appear in use. Blood sample 192 is loaded by hand into the input tray 194. The axial separation module sequentially accepts sample tubes from input tray 194 and processes them. After each sample is separated, it is ejected to the output tray 196. The blood separation process is initiated by loading a tube (or tubes) into the input tray. Once the process has been initiated no further user intervention is required except removing processed samples from output tray 196. Any deviations from the expected vibration or temperature level of the sample are detected by the control and sensing circuit of FIG. 10 which then interrupts operation of the machine and sounds an alarm. Once the separation process is complete and a sample tube has been ejected to output tray 196, serum or plasma may be extracted from the processed blood collection tube either by conventional methods or by using the fluid dispensing apparatus of this invention (shown in FIGS. 8a through 8c).

Since many changes can be made in construction of the above sample collection and separation containers, axial separation module, and applications of the machine and process of this invention without departing from the scope thereof, it is intended that all matter contained in the above description or shown in the accompanying drawings shall be interpreted as illustrative and not in a limiting sense. Examples of embodiments which do not depart from the scope of this disclosure are: a change in construction of the closure segment which does not affect the operation of the separable joint (herein described) between the closure segment and separator assembly; modification of the separating element to facilitate its construction from a single component; the addition of blood clot activators or anticoagulants to the sample containers; modification of the tubular chamber to replace the attachment lip with a self-tapping thread, bayonet lock, or other mechanical connection means; the addition of a filtering element to the fluid dispensing apparatus to filter fibrin from a separated serum sample; or, modification of the axial separation module to use a different drive/bearing combination. Accordingly the invention is to be limited only by reference to the appended claims.

We claim:

1. A separating apparatus positionable within a liquid-carrying tube for partitioning phases of the liquid that are ordered about the longitudinal axis of the tube, the apparatus comprising:

a first portion slidable within a tube to divide the tube interior into a first chamber and a second chamber, whereby there is no fluid communication between the first and second chambers; and a second portion attached to the first portion and configured to define an intermediate space within the separating apparatus, the second portion having a passage formed therethrough for permitting fluid communication between the intermediate space and the first chamber without permitting fluid communication between the intermediate space and the second chamber.

2. The apparatus of claim 1 wherein the passage is continuously open irrespective of whether the tube is moving or stationary.

3. A separating apparatus positionable during a separation process within a liquid-carrying tube for partitioning phases of the liquid that are ordered about the longitudinal axis of the tube, the apparatus comprising:

a portion formed of substantially transparent material and slidable within a tube to divide the tube interior into a first chamber and a second chamber, the portion having a longitudinal axis that is substantially collinear with the longitudinal axis of the tube within which the apparatus is positioned; and the portion having a passage formed therein to be in fluid communication with the first chamber, the passage having a central part through which the longitudinal axis of the apparatus extends, and at least one slotted part contiguous with and extending radially away from the central part of the passage.

4. The apparatus of claim 3 wherein the size of the passage is fixed.

5. A separating apparatus positionable during a separation process within a liquid-carrying tube for partitioning phases of the liquid that are ordered about the longitudinal axis of the tube, the apparatus comprising:

a substantially transparent portion slidable within a tube to divide the tube interior into a first chamber and a second chamber, the portion having a longitudinal axis that is substantially collinear with the longitudinal axis of the tube within which the apparatus is positioned;

the portion having a passage formed therein to be in fluid communication with the first chamber, the passage having a central part through which the longitudinal axis of the apparatus extends; and means for constraining light that is directed radially toward the portion to pass radially through the central part of the passage.

6. A dispensing apparatus for dispensing fluid from a container that has a pierceable closure fitted within an opening in the container, the apparatus comprising:

a plate having a first side and a second side, the first side of the plate having a tubular member attached thereto, the tubular member having one end configured for piercing through the closure;

fastening means for securing the plate relative to the container with the tubular member pierced through the closure;

a flexible receptacle attached to the plate to extend from the second side of the plate, the interior of the receptacle being in fluid communication with the interior of the tubular member so that fluid may flow between the container and the receptacle; and a normally closed orifice formed in the receptacle, the orifice being opened whenever the flexible receptacle is squeezed.

* * * * *